United States Patent [19]

Hass

[11] 4,273,532

[45] Jun. 16, 1981

[54] EDENTULOUS IMPRESSION CORRELATOR AND METHOD OF USING SAME

[76] Inventor: Martin A. Hass, 1105 El Medio Dr., Pacific Palisades, Calif. 90272

[21] Appl. No.: 75,753

[22] Filed: Sep. 14, 1979

[51] Int. Cl.$^3$ .............................................. A61C 9/00
[52] U.S. Cl. ........................................ 433/37; 433/43
[58] Field of Search ....................... 433/43, 41, 42, 46, 433/37, 44, 45, 47, 72, 75, 229

[56] References Cited

U.S. PATENT DOCUMENTS

| | | | |
|---|---|---|---|
| 252,785 | 1/1882 | Manker | 433/44 |
| 760,295 | 5/1904 | Allen | 433/42 |
| 957,563 | 5/1910 | Kerr | 433/46 |
| 2,001,963 | 5/1935 | Keller | 433/42 |
| 2,299,285 | 10/1942 | Taylor, Jr. | 433/44 |
| 3,084,435 | 4/1963 | Hass et al. | 433/229 |

FOREIGN PATENT DOCUMENTS 333897 2/1929 United Kingdom ...................... 433/43

*Primary Examiner*—Gene Mancene
*Assistant Examiner*—John J. Wilson
*Attorney, Agent, or Firm*—Fulwider, Patton, Rieber, Lee & Utecht

[57] ABSTRACT

An edentulous impression correlator includes a support of adjustable configuration and a handle. The support is adjusted to fit an individual patient's mouth and a quantity of impressionable material placed on it. Then the support and material is positioned within the patient's mouth, with the handle protruding, and an impression is made to form a bite record including the upper vault and the lower ridge crest. The support is removed from the mouth and the material is removed from the support by sliding it over the handle.

7 Claims, 6 Drawing Figures

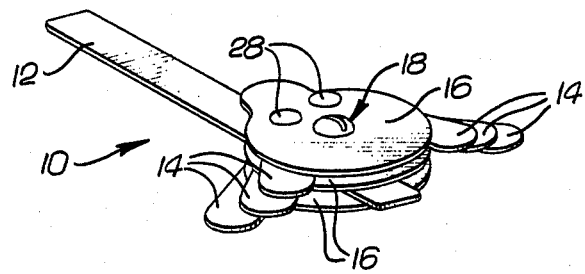
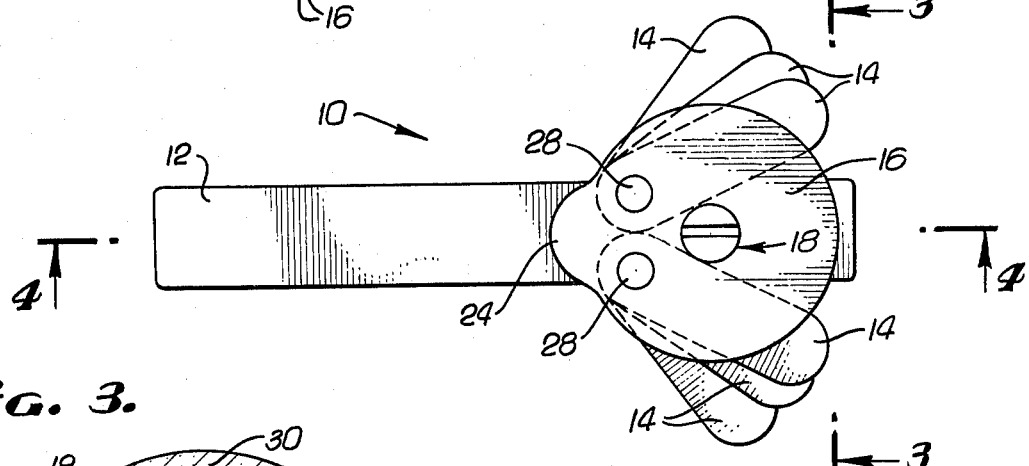
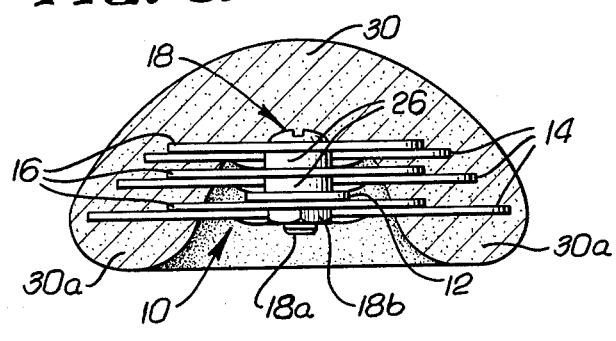
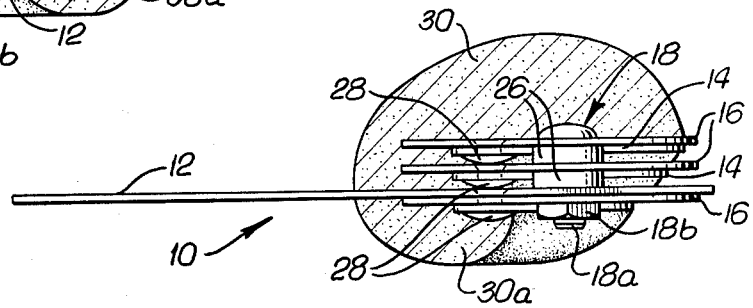
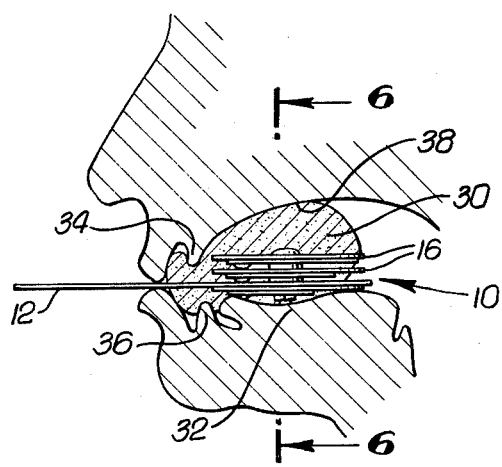
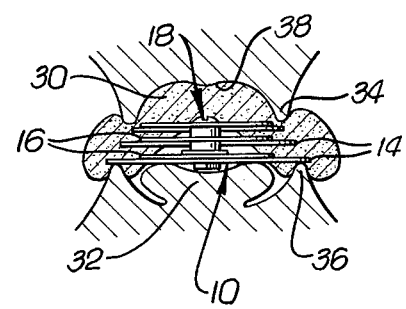

EDENTULOUS IMPRESSION CORRELATOR AND METHOD OF USING SAME

FIELD OF THE INVENTION

The present invention relates to recording the bite of a patient to be fitted with dentures, and more particularly, to a device and method for holding impressionable material within the mouth of the patient while such a record is made.

BACKGROUND OF THE INVENTION

When a patient is fitted for artificial dentures, it is necessary to make a record of his bite which correlates the relative positions of the maxilla (upper arch) and mandible (lower arch). This record is then used by a technician to articulate stone models of the teeth in proper vertical and horizontal relation to make bite blocks and wax rims with accuracy. If desired, the anterior teeth can be set from this bite record using center line and lip markings.

According to conventional dental procedure, a record of the bite is made by placing in the patient's mouth a quantity of impressionable material such as wax or silicone putty. The patient then closes his jaw to the proper vertical position as desired by the dentist and the material is allowed to set before it is removed. Enough material should be inserted to get a full impression of the lower ridge crest and the upper vault. The mouth is thus relatively full and the material interferes with the natural position of the tongue, making it difficult to be sure that the upper vault and lower ridge crest are properly correlated (oriented). The procedure may be further complicated by the patient's fear, either real or imagined, that the material might slide down into this throat, causing him to choke.

It is a principal objective of the present invention to improve upon the conventional procedure for taking a bite impression and to provide a new device for use in this procedure.

SUMMARY OF THE INVENTION

According to the present invention, the conventional procedure for taking a bite impression is modified by providing a device, termed an edentulous impression correlator, for insertion in the patient's mouth to carry the impressionable material.

The device of the invention includes an arm that serves as a handle and a support for the impressionable material attached to one end of the arm. Preferably, the support extends outwardly and forwardly from the arm, thereby conforming to the shape of the mouth and preventing the material from sliding off the support in the direction of the throat. The support is tappered from a relatively wide base, generally conforming to the lower ridge crest, to a relatively narrow top, generally conforming to the upper vault. Movable components used to form the support can be secured in a configuration that fits the mouth of a particular patient.

In a preferred device according to the invention, the support is formed by wings arranged in pairs of V-shaped configuration. The wing pairs are stacked horizontally, and the lower most pair is preferably closest to the arm. Three pairs of wings are generally optimum.

To hold the wings of a preferred embodiment of the invention in properly adjusted positions, giving the support the desired overall configuration, a holding plate overlies each pair of wings. The plates are pressed together to clamp the wings in position.

According to the method of the invention, impressionable material is placed on the support which is then positioned in the patient's mouth. After an impression has been formed, the support and material are removed by the arm that projects from the patient's mouth. After a bite record has been formed as an impression on the material and the material has set, the support and material are removed from the mouth together. The material is then separated from the support by sliding it over the handle.

Preferably, the support is adjusted to fit the patient's mouth by pivotal movement of the wings before it is inserted. The material should cover the top of the support to fill the upper vault and should cover a portion of the bottom of the vault conforming to the lower ridge crest.

Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 1 is a perspective view of edentulous impression correlator constructed in accordance with the present invention;

FIG. 2 is a plan view of the device of FIG. 1;

FIG. 3 is an elevational view of the device of FIG. 1 with impressionable material added taken substantially as indicated by the arrows 3 of FIG. 1;

FIG. 4 is a cross-sectional view of the device of FIG. 1 with impressionable material added taken substantially as indicated by the arrows 4 of FIG. 2;

FIG. 5 is a cross-sectional side view of the device of FIG. 1 and impressionable material positioned within the mouth of a patient; and FIG. 6 is another cross-sectional view taken substantially as indicated by the arrows 6 of FIG. 5, showing the device of FIG. 1 and impressionable material positioned within the mouth of a patient.

DESCRIPTION OF THE PREFERRED EMBODIMENT

An edentulous impression correlator 10, shown in FIGS. 1–6 of the accompanying drawings, is an exemplary device constructed in accordance with the present invention and suitable for practicing the method of the invention. In general, it includes an arm 12, a plurality of wings 14 a plurality of holding plates 16, and a screw fastener 18 for pressing the plates together to hold the wings in selected positions.

The arm 12 is a flat, elongated metal strip that serves as a handle. Near one end of the arm 12 is an aperture that receives the screw fastener 18 which includes a bolt 18(a) perpendicular to the arm and threadedly engaged by a smooth convex nut 18(b) at the bottom.

The screw fastener 18 secures the holding plates 16, each of which has an aperture through which the bolt 18(a) passes. The holding plates 16 are flat metal pieces having generally accurate edges and, in fact, form circles except for small rounded protrusions 24 extending back along the arm 12. A pair of washer-like spacers 26 encircle the bolt 18, each spacer being located between two holding plates 16. The arm 12 is held between the lower spacer 26 and the top of the lower most plate 16.

Each holding plate 16 carries a pair of the wings 14 arranged in a V-shaped configuration, the wings being pivotably attached to the underside of the plate by rivet-like pivot fasteners 28. The pivot fasteners 28 of the lowest pair of wings 14 also pass through the arm 12. These pivot fasteners 28 are located behind the screw fastener 18. Although the pivot fasteners 28 of a pair of wings 14 are closely spaced, the wings 14 have rounded inner ends that permit them to move without interfering with each other. The wings 14, being flat, easily fit within the horizontal spaces between the plates 16, the height of these spaces being determined by the dimensions of the spacers 26.

It is possible to clamp the wings 14 in selected pivotal positions by tightening the screw fasteners 18. This causes a head on the bottom of each pivot fastener 28 to be pushed upwardly by the top of the holding plate 16 below until the pivot fastener binds. The wing 14 is thus clamped between the head of the fastener 28 and the underside of the plate 16 to which it is attached.

The first step in taking a bite impression is to properly position the wings 14 to fit the mouth of the particular patient. Thus the wings 14 are pivoted to form a smaller angle between them for a patient with a small mouth, while this angle is increased for a person with a large mouth. The lower most pair of wings 14 forms the largest angle and the upper most pair forms the smallest angle. Of course, the wings 14 should be adjusted so that the correlator 10 is symmetrical about the centerline of the arm 12. In this way a triangular support is formed that has a relatively broad base generally conforming to the lower ridge crest and tapers toward a relatively narrow top that generally conforms to the shape of the upper vault.

A suitable quantity of impressionable material 30 is roughly molded over the support formed by the wings 14 so that it covers the top of the support to get a good impression of the upper vault and palate (see FIGS. 3 and 4). The material 30 extends between the wings 14 and between the plates 16 so that it is securely retained. A portion 30a of the material 30 is rolled under the outer edge of the lower most pair of wings 14 to form a U-shape. Preferably, a quick setting silicone putty is used. The material 30 and the supporting portion of the correlator 10 is placed in the patient's mouth with the handle 12 projecting from between the lips, as shown in FIG. 6.

Considerably less material 30 is used than would be required if the correlator 10 were not employed. The patient is more comfortable because the material 30 does not intrude into the area surrounding the tongue 32 to the same extent that it otherwise would. It is impossible for the material 30 to slide off the correlator 10 in the direction of the throat since the wings 14 extend forwardly and outwardly from the end of the arm 12.

As the patient moves the lower jaw to the proper position, the material 30 makes an impression of the maxilla 34 and mandible 36 as well as the palate and upper vault area 38. After the material 30 has set, the correlator 10 is grasped by the protruding arm 12 and removed from the patient's mouth. The material 30 can then be easily removed from the correlator 10 by sliding it off over the arm 12. Thus the material 30 can be sent to a dental lab while the correlator 10 is retained for future use.

When the method and device of the present invention is used, the procedure for creating a bite record is simplified considerably. Not only is the time of the dentist conserved, but the number of required visits by the patient is reduced. The job of the laboratory is also made easier and less time consuming because a better, more accurate impression is obtained.

It will be appreciated that the present invention uniquely combines the advantages of being compact, light weight, inexpensively manufactured and easily installed. While a preferred embodiment of the invention has been shown and described, it will be appreciated that many changes and modifications may be made without departing from the spirit and scope of the invention.

I claim:

1. An edentulous impression correlator comprising:
    an arm that serves as a handle and is adapted to project from a patient's mouth; and
    at least three pairs of wings forming a support for impressionable material, said wings having horizontal surfaces extending outwardly and forwardly from said arm when in a patient's mouth, said wings being arranged in pairs that are stacked horizontally, the wings of each pair having a generally V-shaped configuration, and the wings of the lower-most of said pairs being closest to said arm and forming the largest angle therebetween.

2. The edentulous impression correlator of claim 1 wherein each successively higher pair of wings forms a smaller angle than the pair below, whereby said wings form a support that is tappered from a relatively wide base generally corresponding to the lower ridge crest and a relatively narrow top generally corresponding to the upper vault.

3. The edentulous impression correlator of claim 2 further comprising means for adjustably securing said wings in selected angular positions to fit the mouth of a particular patient.

4. The edentulous impression correlator comprising:
    an arm that serves as a handle and is adapted to project from a patient's mouth; and
    at least three pairs of wings forming a support for impressionable material, said wings having horizontal surfaces extending outwardly and forwardly from said arm when in a patient's mouth, said wings being arranged in pairs that are stacked horizontally, the wings of each pair having a generally V-shaped configuration; and
    adjustment means for securing said wings in selected angular positions to fit the mouth of an individual patient.

5. The edentulous impression correlator of claim 4 wherein the lower most of said pairs is closest to said arm.

6. The edentulous impression correlator comprising:
    an arm that serves as a handle and is adapted to project from a patient's mounth; and
    a plurality of wings forming a support for impressionable material, said wings having horizontal surfaces extending outwardly and forwardly from said arm when in a patient's mounth, said wings being arranged in pairs that are stacked horizontally, the wings of each pair having a generally V-shaped configuration; and
    adjustment means for securing said wings in selected angular positions to fit the mouth of an individual patient, said adjustment means comprising a plurality of holding plates, means for pivotably mounting said wings on said plates, and means for pressing said plates together, thereby preventing pivotal movement of said wings.

7. An edentulous impression correlator comprising:
a handle adapted to project from a patient's mouth;
a plurality of wings forming a support for impressionable material, said wings having horizontal surfaces adapted to extend away from said handle into a patient's mouth, said wings being arranged in pairs that are stacked horizontally, the wings of each pair being adapted to form a generally V-shaped configuration with the wings of the lower most of said pairs forming the largest angle therebetween; and means for adjustably securing said wings in selected angular positions to fit the mouth of a particular patient.

* * * * *